United States Patent [19]

Cymbaluk et al.

[11] Patent Number: 4,599,469
[45] Date of Patent: Jul. 8, 1986

[54] HYDROGENATION PROCESS

[75] Inventors: Ted H. Cymbaluk; Jim D. Byers; Marvin M. Johnson, all of Bartlesville, Okla.

[73] Assignee: Phillips Petroleum Company, Bartlesville, Okla.

[21] Appl. No.: 614,891

[22] Filed: May 29, 1984

[51] Int. Cl.$^4$ ............................................. C07C 21/24
[52] U.S. Cl. .................................... 570/193; 260/404; 260/409; 260/410.9 N; 560/128; 560/211; 560/261; 562/495; 562/512; 562/592; 562/599; 568/462; 570/200; 570/216
[58] Field of Search ...................... 568/462, 468, 467; 570/137, 135, 193, 200, 216; 562/405, 512, 599, 485; 560/211, 128, 122–124, 261, 113, 1; 260/404, 409, 410.9 R

[56] References Cited

U.S. PATENT DOCUMENTS

| 2,334,091 | 11/1943 | Herstein | 568/449 |
|---|---|---|---|
| 3,293,290 | 12/1966 | Flint et al. | 568/475 |
| 3,322,686 | 5/1967 | Brown | 252/432 |
| 3,418,376 | 12/1968 | Tan | 568/449 |
| 3,654,358 | 4/1972 | Jeffrey | 568/470 |
| 3,971,831 | 7/1976 | Mourier | 568/462 |
| 4,018,831 | 4/1977 | Bowes et al. | 568/462 |
| 4,036,836 | 7/1977 | Greene | 546/290 |
| 4,125,735 | 11/1978 | Close | 560/261 |
| 4,163,750 | 8/1979 | Bird et al. | 260/409 |
| 4,188,333 | 2/1980 | Cahen | 260/409 |
| 4,361,705 | 11/1982 | Marcelin et al. | 568/462 |
| 4,394,525 | 7/1983 | Vogel et al. | 568/462 |
| 4,474,907 | 10/1984 | Rao | 568/470 |

FOREIGN PATENT DOCUMENTS

| 256304 | 5/1963 | Australia | 568/470 |
|---|---|---|---|
| 0040829 | 12/1981 | European Pat. Off. | 570/216 |
| 2062522 | 6/1971 | Fed. Rep. of Germany | 568/470 |
| 376206 | 7/1932 | United Kingdom | 568/449 |
| 960195 | 6/1964 | United Kingdom | 568/449 |

OTHER PUBLICATIONS

Brown et al., "J. Amer. Chem. Soc." vol. 85, p. 1003 (1963).
Brown et al., "J. Amer. Chem. Soc." vol. 85, p. 1005 (1963).

Primary Examiner—Werren B. Lone
Attorney, Agent, or Firm—Stephen E. Reiter

[57] ABSTRACT

Process for the hydrogenation of functionally substituted acetylenic compounds employing catalyst comprising nickel boride on an inorganic oxide support is disclosed. Functionally-substituted acetylenic compounds are selectively reduced under mild reaction conditions to give functionally-substituted cis-olefinic compounds in high yield.

22 Claims, No Drawings

HYDROGENATION PROCESS

BACKGROUND OF THE INVENTION

This invention relates to hydrogenation processes. In another aspect, the invention relates to hydrogenation of acetylenic compounds. In a further aspect, the invention relates to the stereospecific hydrogenation of acetylenic compounds.

For a hydrogenation process to be useful on a large scale, catalysts must be available which are readily and inexpensively prepared, give selective reaction, and have high reactivity over an extended period of time. Prior art hydrogenation catalysts employed for the hydrogenation of functionally-substituted acetylenic compounds have a variety of drawbacks which prevent their use on a large scale. Thus, for example, catalysts employing platinum or palladium are very expensive and readily lose activity in the presence of various functional groups; the preparation of catalysts such as Raney nickel is a relatively tedious process. In addition, some hydrogenation catalysts display low reactivity with functionally-substituted acetylenic compounds. Where prior art hydrogenation catalysts display high reactivity with functionally-substituted acetylenic compounds, a frequent problem is poor selectivity to the desired hydrogenated product, due, for example, to double-bond isomerization of the initially formed olefinic product, and/or undesired side reactions between the hydrogenation catalyst and the functional group of the reactant acetylenic compound (or product olefinic and/or aliphatic compounds).

OBJECT OF THE INVENTION

An object of the invention is a process to selectively hydrogenate the carbon-carbon triple bond of functionally-substituted acetylenic compounds to give functionally-substituted cis-olefinic compounds.

Another object of the invention is a hydrogenation process for the conversion of functionally-substituted acetylenic compounds employing easily prepared, inexpensive and selective hydrogenation catalysts.

These and other objects of our invention will become apparent from the disclosure and claims herein provided.

SUMMARY OF THE INVENTION

In accordance with the present invention, a process is provided comprising contacting a functionally-substituted acetylenic compound with hydrogen and a catalyst comprising nickel boride on an inorganic oxide support. A functionally-substituted cis-olefinic compound is obtained.

In accordance with another embodiment of the invention, a cis-olefinic halide is prepared by reaction of an α,ω-dihalide with a metal acetylide to give an acetylenic halide, then the acetylenic halide is contacted with hydrogen in the presence of a selective hydrogenation catalyst comprising nickel boride on an inorganic oxide support.

In accordance with yet another embodiment of the invention, a cis-olefinic aldehyde is prepared by reaction of an α,ω-dihalide with a metal acetylide to give an acetylenic halide, then the acetylenic halide is either (i) contacted with hydrogen and a selective hydrogenation catalyst comprising nickel boride on an inorganic oxide support followed by oxidation of the halide to give the desired cis-olefinic aldehyde or (ii) oxidized to give an acetylenic aldehyde followed by contacting of the acetylenic aldehyde with hydrogen and a selective hydrogenation catalyst comprising nickel boride on an inorganic oxide support to give the desired cis-olefinic aldehyde.

DETAILED DESCRIPTION

Catalyst

The nickel boride on an inorganic oxide support employed in the practice of the present invention may be prepared by various methods known to those skilled in the art. For example, catalyst may be conveniently prepared by contacting at least one nickel compound and at least one borohydride compound in a suitable solvent in the presence of inorganic oxide support. The conditions under which catalyst components are contacted are not critical. Satisfactory results are obtained by contacting the components at room temperature. Since contact with oxygen is detrimental to the catalyst, it is preferred to prepare and store the catalysts described herein under an inert gas atmosphere or hydrogen atmosphere for extended catalyst lifetimes. After the catalyst components have been thoroughly blended, solvent can be removed by reduced pressure distillation to provide a concentrated catalyst slurry or paste for subsequent use.

Suitable solvents for use in the preparation of the nickel boride on inorganic oxide support are solvents which have an appreciable capacity for dissolution of nickel compounds and borohydride compounds, as well as the ability to wet the surface of the inorganic oxide supports employed in the practice of the invention. Solvents which satisfy the above criteria include, but are not limited to, water, alcohols, esters, ethers (including cyclic ethers) and the like.

Alcohols which are useful have the general formula

wherein R' is $C_1$ through $C_{10}$ alkyl, cycloalkyl, aryl, aralkyl or alkaryl. Exemplary alcohols include methanol, ethanol, butanol and the like.

Esters which are useful have the general formula

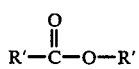

wherein each R' is independently defined as above. Preferably, esters employed in the practice of the invention have 3 up to about 12 carbon atoms. Exemplary esters include methyl acetate, ethyl acetate, butyl acetate, methyl propionate and the like.

Ethers which are useful have the general formulae

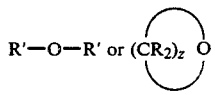

wherein each R' is independently defined as above, each R is independently H, $C_1$ through $C_{20}$ alkyl, cycloalkyl, aryl, aralkyl and alkaryl, and $z = 3$ through 11. Preferably, ethers employed in the practice of the invention have about 4 up to about 12 carbon atoms. Exemplary ethers include diethyl ether, diphenyl ether, tetrahydrofuran (THF) and the like.

The volume of solvent employed for catalyst preparation is not critical. However, it must be recognized that extremely large volumes of solvent are undesirable because of the energy required for subsequent solvent removal. In addition, extremely small volumes of solvent are undesirable because insufficient solid/liquid contact may result.

Suitable nickel compounds for use in the preparation of nickel boride on inorganic oxide support are compounds which are at least sparingly soluble in the solvents indicated above. Exemplary nickel compounds include, but are not limited to, nickel acetate, nickel fluoride, nickel chloride, nickel bromide, nickel iodide, nickel nitrate, nickel sulfate, nickel acetylacetonate and the like, and mixtures of any two or more thereof.

Suitable borohydride compounds for use in the preparation of nickel boride on inorganic oxide support are compounds which are at least sparingly soluble in the solvents indicated above. Exemplary compounds conform to the formula:

$$M(BH_4)_n$$

where M is a monovalent or divalent cation selected from the group consisting of quaternary ammonium cations ($NR_4'-$, wherein each R' is independently $C_1$ through $C_{10}$ alkyl, cycloalkyl, aryl, aralkyl and alkaryl), alkaline earth metals and alkali metals. Where M is a monovalent cation, $n = 1$. Where M is a divalent cation, $n = 2$. Examples of useful borohydride compounds are lithium borohydride, sodium borohydride, potassium borohydride, magnesium borohydride, calcium borohydride and tetraethyl ammonium borohydride.

The term inorganic oxide support is intended to include those support materials which are useful for the preparation of heterogeneous catalysts. Suitable support materials include, but are not limited to, silica, alumina, silica-alumina, aluminum phosphate, zirconium phosphate, titanium phosphate, calcium phosphate, magnesium phosphate, magnesia-titania, thoria, titania, zirconia, and the like as well as mixtures of any two or more thereof. Silica is a presently preferred support because of its ready availability, ease of handling and resultant good activity of catalysts prepared with silica as support.

Solutions of at least one nickel compound and at least one borohydride compound are conveniently contacted at about room temperature in the presence of one or more inorganic oxide supports, although contacting may take place at temperatures from about 0° C. up to about 100° C. Any of the numerous techniques known to those skilled in the art for contacting solids and liquids may suitably be employed. The molar ratio of the nickel boride components employed can vary over a wide range, with molar ratios of borohydride compound to nickel compound ranging from about 1:1 to about 12:1 most commonly being employed.

The proportion of nickel boride combined with the inorganic oxide support can vary appreciably, but generally the support will contain at least about 0.1% by weight of the nickel metal, based on the total weight of support plus nickel boride and calculated as nickel metal. Generally the support will contain an upper limit of about 40% by weight of the nickel metal, based on the total weight of support plus nickel boride and calculated as nickel metal. Amounts of about 0.2 to about 20% by weight of the nickel metal, calculated as nickel metal and based on the total weight of support plus nickel boride are preferred, with amounts of about 1 to about 10% by weight of the nickel metal, calculated as nickel metal and based on the total weight of support plus nickel boride are especially preferred because excellent catalyst reactivities and product selectivities are obtained.

Substrate

The term "functionally-substituted acetylenic compounds" as employed herein is intended to include organic molecules containing at least one carbon-carbon triple bond and at least one functional group selected from the following:

$$-Br, \quad -I, \quad -CO_2R, \quad -O\overset{O}{\underset{\|}{C}}R, \quad -\overset{O}{\underset{\|}{C}}-NR_2,$$

and the like and mixtures of any two or more thereof (where each R is independently H, $C_1$ through $C_{20}$ alkyl, cycloalkyl, aryl, aralkyl and alkaryl). Preferred functional groups are the halides, i.e., chloride, bromide and iodide, with the bromide being most preferred.

An especially preferred functionally-substituted acetylenic compound for use in the practice of the invention is prepared by contacting an $\alpha,\omega$-dihalide with a metal acetylide. Thus, for example, an $\alpha,\omega$-dihalide having the following general formula $$Z-CH_2-(CR_2)_y-CH_2-Z$$

(where y is broadly 1 through 20, and preferably 1 through 10; Z is Cl, Br or I and R is as defined above) can be reacted with a metal acetylide. A variety of such $\alpha,\omega$-dihalides can be prepared from suitable starting materials such as, for example, $\alpha,\omega$-diols and $\alpha,\omega$-dienes by methods well known in the art such as, for example, addition of gaseous or aqueous hydrogen halide to an $\alpha,\omega$-diol or addition of gaseous hydrogen halide to an $\alpha,\omega$-diene in the presence of a peroxide.

The metal acetylide employed can be prepared from an acetylene compound of the following general formula:

$$H-C\equiv C-CH_2-(CR_2)_x-H$$

where x is broadly 0-20 and preferably 0-10 and R is as defined above. Although any suitable metallating agent can be employed, preferred compounds include those, for example, of the structure R″Me, where:
R″=C$_1$-C$_4$ hydrocarbyl or NH$_2$, and
Me=Li, Na.
The resulting metal acetylide has the formula:

Me—C≡C—CH$_2$—(CR$_2$)$_x$—H where x, R and Me are as defined previously.

Promoters are desirable to increase the rate of the desired condensation reaction. Some examples of operable donor compounds include ethylene diamine, tetramethylenediamine, tetramethylurea, pyridine, dioxane and the like. Preferred donor compounds ae diglyme (diethylene glycol dimethyl ether), triglyme (triethylene glycol dimethyl ether), tetraglyme (tetraethylene glycol dimethyl ether), hexamethylphosphorus triamide, 1,3-dimethyl-3,4,5,6-tetrahydro-2(1H)-pyrimidinone and 1,3-dimethyl-2-imidazolidinone and mixtures thereof.

Solvents such as tetrahydrofuran (THF) can optionally be employed. When used, solvents are preferably dried prior to use such as, for example, by percolation through a bed of Alcoa H151 Alumina.

Although any ratio of α,ω-dihalide to acetylene compound is operable, the ratio of α,ω-dihalide to acetylene compound employed is generally maintained above one to minimize the formation of diacetylide product. Preferably, α,ω-dihalide to acetylene compound ratios of 1:1 to about 4:1 are employed. Most preferably, ratios of about 1.1:1 to about 2:1 are used.

Although any suitable amount of metallating agent can be employed, for best results, the metallating agent, such as R″Me, is generally employed in about equimolar amounts relative to the acetylene compound charged. Typically, the metallating agent is added slowly to a chilled (below about 10° C.) solution of the acetylene compound in a solvent such as THF, diglyme or the like.

The promoter, when employed, is charged in any amount, although it is preferably employed in the amount of about 0.5-1 mole per mole of metallating agent when added solvent is also present. When the promoter is also used as solvent, e.g. diglyme, it is preferably charged in the amount of about 2-4 moles per mole of metallating agent.

The reaction of the α,ω-dihalide and the metal acetylide can be carried out at any suitable temperature and for any appropriate time as can be readily determined by one skilled in the art. Typical reaction conditions employed include a preferred temperature range of about 90°-150° C., with 100°-110° C. most preferred. Suitable reaction time is about 2-8 hours, with 3-5 hours preferred. Reaction generally is carried out at atmospheric pressure, although most any pressure can be employed. It is desirable, although not essential, that reaction be carried out under an inert atmosphere, employing an inert gas such as N$_2$, Ar or the like.

Any suitable method for product isolation can be employed. A typical reaction workup involves first adding water, then separating the organic phase and distilling. Alternatively, a nominal amount of water can be added to hydrolyze active metal species, thereby eliminating the need for a phase separation. Thus, once the required minimal amount of water is added, the reaction mixture can be distilled directly. The product acetylenic halide can be subjected to hydrogenation conditions in accordance with the invention, or the remaining halogen functional group can be further converted before hydrogenation of the acetylenic function.

For example, the halide can be hydrolyzed to an alcohol, which can be oxidized to give an aldehyde or an acid, or esterified to give an acetylenic ester. A preferred conversion is the one-step oxidation of the halide to give an aldehyde. The one-step oxidation of acetylenic halide to acetylenic aldehyde can be carried out by contacting acetylenic halide, sodium bicarbonate, an amine oxide and, optionally, a solvent.

Amine oxides in general are suitable for the one-step oxidation reaction. Preferred compounds include pyridine N-oxide, trimethylamine N-oxide, and triethylamine N-oxide.

Suitable solvents for the one-step oxidation of halide to aldehyde include the glymes, such as glyme, diglyme, triglyme, and tetraglyme; aromatics, such as toluene and xylenes; C$_8$ through C$_{14}$ saturated hydrocarbons such as decane; ethers such as THF; polar aprotic solvents such as dimethylformamide (DMF), dimethylsulfoxide (DMSO) and sulfolane.

Any suitable amount of amine oxide as can be readily determined by one skilled in the art can be employed. Typically, a 1:1 to about 4:1 mole ratio of amine oxide to substrate is employed, with ratios of about 1.2:1 to about 2:1 preferred. NaHCO$_3$ can be employed in any suitable amount. Preferably, NaHCO$_3$ will be employed in the range of about 1:1 to about 4:1 NaHCO$_3$ to substrate. It is especially preferred that NaHCO$_3$ be employed in an amount at least twice the molar amount of substrate employed. This is because the NaHCO$_3$ disproportionates under typical reaction conditions to give Na$_2$CO$_3$ and H$_2$O and CO$_2$. Thus, up to one-half of the reactant, NaHCO$_3$, charged to the reaction may become unavailable for the desired oxidation reaction.

When the acetylenic halide starting material is a chloride (Z=Cl), sodium iodide (NaI) may additionally be provided in the reaction mixture. Addition of NaI in any suitable amount, preferably from about 1 to about 10 mol % based on acetylenic halide substrate, serves to enhance the rate of the oxidation reaction.

When solvent is employed, any suitable ratio of solvent and acetylenic ahlide substrate can be used. Generally, about a 3:1 to about 1:3 solvent to substrate ratio is employed.

Reaction is preferably, although not necessarily, carried out at atmospheric pressure under an inert atmosphere (N$_2$, Ar or the like). Any suitable temperature and pressure may be employed. Temperatures employed are preferably about 90°-150° C., with 105° to about 130° C. most preferred. Any reaction time is suitable, although generally reaction times of 30 minutes to about 8 hours are employed, with about 1-3 hours preferred.

Any suitable method as known by those skilled in the art can be employed for product isolation. A typical reaction workup involves several steps. First, reaction mixture is cooled to about 25° C. to precipitate solid materials. An equal volume of a suitable organic solvent such as ethyl acetate or diethyl ether is added, and the mixture filtered. The solid-free liquid is washed once with an equal volume of water. Crude product acetylenic aldehyde is then ready for solvent removal by, for example, distillation. Clean product is then recovered, typically by distillation at reduced pressure.

Hydrogenation

Hydrogenation in accordance with the present invention can be carried out on any of the functionally-substituted acetylenic compounds previously described. It should of course also be recognized that hydrogenation of, for example, an acetylenic halide to give an olefinic halide can be followed by a one-step oxidation as described above to give an olefinic aldehyde. Thus, a wide variety of olefinic products can be prepared according to the invention by converting one functional group to another either before or after the inventive hydrogenation step is carried out.

In accordance with the present invention, functionally-substituted acetylenic compounds are selectively hydrogenated to give functionally-substituted cis-olefinic products. Selective hydrogenation refers to the amount of hydrogen consumed in the hydrogenation reaction, i.e., one mole of hydrogen per mole of acetylenic compound to give an olefin (to the substantial exclusion of the consumption of two moles of hydrogen per mole of acetylene to give an aliphatic compound); to the orientation of hydrogen addition across the acetylenic triple bond where an olefinic product is obtained; and to the presence or absence of double-bond isomerization in the olefinic product obtained by addition of one mole of hydrogen to an acetylenic compound. Selectivities of at least 90% by weight to functionally-substituted cis-olefinic products are desirable, with less than about 5% by weight of trans-olefinic product and less than about 5% by weight of saturated (i.e., aliphatic) product. Preferably, selectivities of at least about 95% by weight of functionally-substituted cis-olefinic products will be obtained, with less than about 3% by weight each of trans-olefinic product or saturated product.

Reaction parameters include a preferred reaction pressure of atmospheric to about 200 psig, although most any pressure can be employed. Suitable reaction temperatures include about 0° C. to about 150° C. with temperature preferably maintained between about 20° and about 100° C. Most preferably, a reaction temperature of 30° to about 50° C. will be employed. Reaction time can broadly be 30 minutes to about 8 hours, with 60 minutes to about 120 minutes preferred.

Solvent and substrate can be employed in any suitable ratio as readily determined by one skilled in the art. Suitable ratios are about 10:1 to about 1:10 parts by volume of solvent to substrate. Preferably, for ease of handling and product recovery, solvent and substrate are charged to the reactor in roughly equal volumes.

The total amount of catalyst to be used can be readily determined by one skilled in the art. Preferably, the amount of catalyst employed, expressed as the molar ratio of functionally-substituted acetylenic compound changed to the nickel metal in the supported nickel boride catalyst, ranges from about 1:1 to about 300:1. Most preferably a molar ratio ranging from about 5:1 to about 100:1 is used, for most efficient use of catalyst and high product selectivities.

Hydrogen is generally fed on demand, i.e., as it is taken up by the reaction mixture. Thus, for example, where reaction is carried out at 120 psig, reactor pressure may be allowed to drop to about 60 psig, then the pressure will be returned to about 120 psig by introducing more hydrogen. Alternatively, reaction may be run at atmospheric pressure with continuous hydrogen uptake from a manometer assembly as hydrogen is consumed by reaction.

Reaction workup consists of catalyst removal, for example, by filtration, to give a filtrate, and solvent removal from the filtrate by such techniques as flash distillation, distillation under reduced pressure, and the like.

A further understanding of the present invention and its advantages will be provided by reference to the following examples.

EXAMPLE I

In this example the preparation of a supported nickel boride hydrogenation catalyst is described. In a plastic flask (capacity about 16 liters) about 9 liters of methanol and 2270 grams of amorphous, precipitated silica were thoroughly mixed. In one run the silica employed was Hi Sil 233 having a specific gravity of about 2.0 and a surface area (BET/$N_2$) of about 60 $m^2/g$, (available from PPG Industries, Pittsburgh, PA); in two other runs the silica employed was Zeosyl 100 having a specific gravity of about 2.0 and a surface area (BET/$N_2$) of about 125-150 $m^2/g$ (available from J. M. Huber Corp., Edison, NJ). Then a solution of 288.6 g (1.2 mol) nickel acetate, i.e., $Ni(OAc)_2 \cdot 4H_2O$ (available from Mallinckrodt, Inc., St. Louis, MO) and 500 mL methanol was added with rapid stirring. After the reactor was flushed with $N_2$, a mixture of 43.88 (1.2 mol) $NaBH_4$ (available from Alpha Corporation, Collierville, TN) and 300 ml methanol was added with stirring. After continued stirring for about 5-20 minutes, the reactor contents were stored under $N_2$. Most of the solvent was vacuum-evaporated from the mixture just prior to the use of the nickel boride catalyst.

EXAMPLE II

This example illustrates the inventive hydrogenation of an alkynyl bromide, $C_4H_9-C{\equiv}C-C_{10}H_{20}Br$ (1-bromo-11-hexadecyne; prepared at Phillips Petroleum Company, Research Center, Bartlesville, OK) in the presence of the supported nickel boride catalyst prepared in Example I.

In a first run, 100 grams (0.33 mol) of n—$C_4H_9-C{\equiv}C-C_{10}H_{20}Br$, 55 grams (~0.03 mol of Ni) of nickel boride/silca-methanol paste, produced as described in Example I, and 200 ml methanol were charged to a stirred 1-liter autoclave, which was first flushed with $N_2$ and with $H_2$. After about 16 minutes at a temperature of about 22° to about 27° C., when pressure had decreased from 120 to about 65 psig, hydrogen gas was added up to a total of 120 psig. The temperature was allowed to rise to about 31° C. A second hydrogen addition followed 9 minutes after the first $H_2$ addition so as to provide a total pressure of about 121 psig. The reaction mixture was stirred at 30°-32° C. for about 13 minutes. Then the reactor was opened, and the reaction product was filtered through a sintered glass funnel so as to remove catalyst material. The filtrate was subjected to vacuum evaporation. About 80 grams of hydrogenated material was recovered. The recovered material was essentially identical to cis-11-hexadecynyl bromide which was prepared by hydrogenation of 1-bromo-11-hexadecyne with prior art catalysts as determined by gas chromatographic (gc), nuclear magnetic resonance (nmr), and infrared (ir) measurements.

In a second run, 55 grams (~0.03 mol of Ni) of the nickel boride/methanol paste produced as described in Example I was vacuum-dried at ambient temperature and was then slurried with about 100 mL alumina-treated n-hexane. This mixture, plus 100 grams (~0.33 mol) of n—$C_4H_9$—C≡C—$C_{10}H_{20}Br$ and 200 ml hexane were placed in the stirred autoclave, which was flushed with $N_2$ and $H_2$. After about 160 minutes during which time the reaction temperature rose from about 22° C. to about 26° C. and reaction pressure fell from about 120 to about 73 psig, $H_2$ was added so as to repressurize the autoclave to 121 psig. About 75 minutes after the first $H_2$ addition, when reaction temperature had increased to about 28° C. more $H_2$ was added to increase reactor pressure to about 120 psig. The reaction mixture was kept at about 30° C. for about 65 minutes after the second addition. Then the autoclave was opened, and the reaction mixture was filtered as described for the first run. About 100 grams of hydrogenated material was recovered (thus indicating essentially complete conversion). As calculated from gas chromatographic data, this material consisted of about 95 weight-% cis-11-hexadecenyl bromide, 2 weight-% of trans-11-hexadecenyl bromide and about 3 weight-% of saturated $C_{16}H_{33}Br$.

A third run was carried out essentially in accordance with the above-described second run, except that the amount of nickel boride catalyst was only 5 grams or ~0.003 mol of Ni (per 100 grams (0.33 mol) of the acetylenic bromide) and the reaction temperature was about 37°-45° C. The hydrogenation reaction gave quantitative conversion of the 1-bromo-11-hexadecyne. Product obtained was essentially identical to the product obtained above, as determined by gc, nmr and ir measurements. When the reaction mixture was not heated above 30° C., no appreciable reaction was observed.

EXAMPLE III

In this example a Group VIII metal boride catalyst and its performance in the control hydrogenation of an acetylenic bromide are described. 4.4 grams of $FeCl_3$ (0.03 mol) were dissolved in 50 mL methanol with gentle heating. 30 grams of Hi Sil silica were slurried in this solution. 40 mL of methanol were also added. The solvent was evaporated at 150° F., and the solid product was covered with methanol after flushing with $N_2$ for 15-20 minutes. Gradually 3.1 grams (0.08 mol) of $NaBH_4$ pellets were added with rapid stirring. The reaction mixture was stirred and refluxed (~65° C.) for about 2 hours, and was then stored under $N_2$ overnight.

A 15 mL sample of this slurry containing $SiO_2$-supported Fe boride catalyst was tested in the hydrogenation of 50 grams (0.17 mole) of 1-bromo-11-hexadecyne, dissolved in 70 grams n-hexane and 10 mL ethanol, at about 50° C./100 psig $H_2$. No reaction occurred.

A second 15 mL sample of the Fe boride catalyst slurry was tested in the hydrogenation of 1-bromo-11-hexadecyne, dissolved in 70 grams n-hexane and 10 mL butanol, at 90°-100° C./100 psig $H_2$ (i.e., at a temperature that was about 50°-70° C. higher than in runs with Ni boride described in Example II). A slow reaction occurred, but even after about 2.5 hours at this high temperature, the reaction had not reached completion (conversion was about 62%). The amount of the cis-1-bromo-11-hexadene (cis-$C_4H_9$—C=CH—$C_{10}H_{20}Br$) in the reaction product was only about 59 weight-%. About 2 weight-% of the reaction product consisted of the trans bromo-hexadecyne, about 1 weight-% consisted of saturates, and about 38 weight-% was unconverted bromo-hexadecyne.

These results illustrate that the iron boride catalyst was not suitable for the selective hydrogenation of an acetylenic halide to the cis-olefinic halide. Based on these results, it is believed that among the Group VIII metal borides only nickel boride, prepared by reaction of a nickel compound (e.g., carboxylate, halide, nitrate, sulfate and the like) with a borohydride (e.g., $NaBH_4$), preferably supported (e.g., by $SiO_2$ or $Al_2O_3$), is an effective catalyst for the selective hydrogenation of acetylenic halides to cis-olefinic halides.

We claim:

1. A process for the preparation of a functionally substituted cis-olefinic compound having the formula:

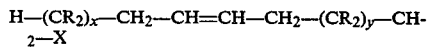

wherein x=0 through 20, y=1 through 20, each R is independently H, $C_1$ through $C_{20}$ alkyl, cycloalkyl, aryl, aralkyl and alkaryl, and X is a functional group selected from the group consisting of:

—Cl,
—Br,
—I,
—$CO_2R$,

—OC—R, and

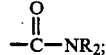

—C—$NR_2$;

where R is as defined above, said process comprising contacting a functionally-substituted acetylenic compound having the formula:

$$H-(CR_2)_x-CH_2-C\equiv C-CH_2-(CR_2)_y-CH_2-X$$

wherein x, y, R and X are as defined above, with hydrogen and a catalyst comprising nickel boride on an inorganic oxide support at a temperature in the range of about 0° to 150° C.; wherein the nickel metal content of said catalyst comprising nickel boride on an inorganic oxide support ranges from about 0.1 to about 40 wt. % based on total weight of support plus nickel boride and calculated as nickel metal; and wherein said inorganic oxide support is selected from the group consisting of:
silica,
alumina,
silica-alumina,
aluminum phosphate,
zirconium phosphate,
titanium phosphate,
calcium phosphate,
magnesium phosphate,
magnesia-titania,
thoria,
titania,
zirconia,
and mixtures of any two or more thereof.

2. A process in accordance with claim 1 wherein x=0 through 10, y=1 through 10, and each R is independently H, $C_1$ through $C_{10}$ alkyl, cycloalkyl, aryl, aralkyl and alkaryl.

3. A process in accordance with claim 1 wherein X is —Cl, —Br or —I.

4. A process in accordance with claim 1 wherein X is —Br.

5. A process in accordance with claim 3 wherein x=3, y=9 and each R is H.

6. A process in accordance with claim 3 wherein x=1, y=9 and each R is H.

7. A process in accordance with claim 3 wherein x=3, y=7 and each R is H.

8. A process in accordance with claim 1, wherein x=5, y=7 and each R is H.

9. A process in accordance with claim 1 wherein said inorganic oxide support is silica.

10. A process in accordance with claim 1 wherein said inorganic oxide support is alumina.

11. A process in accordance with claim 1 wherein said contacting is carried out in the presence of at least one solvent selected from the group consisting of:
alcohols having the general formula R'—OH; wherein R' is $C_1$ through $C_{10}$ alkyl, cycloalkyl, aryl, aralkyl, or alkaryl, esters having the general formula $$R'-\overset{O}{\underset{\|}{C}}-O-R';$$

wherein each R' is independently defined as above, ethers having the general formulae $$R'-O-R' \text{ or } (CR_2)_z\ O$$

wherein each R' is independently defined as above, each R is independently H, $C_1$ through $C_{20}$ alkyl, cycloalkyl, aryl, aralkyl and alkaryl, and z=3 through 11 and mixtures of any two or more thereof.

12. A process in accordance with claim 11 wherein said solvent is methanol.

13. A process in accordance with claim 11 wherein said solvent is tetrahydrofuran.

14. A process in accordance with claim 1 wherein the molar ratio of said funtionally-substituted acetylenic compound to nickel metal in said catalyst comprising nickel boride on an inorganic oxide support is about 1:1 to about 300:1.

15. A process in accordance with claim 1 wherein said hydrogen is provided to the process by partial hydrogen addition throughout the contacting process.

16. A process in accordance with claim 15 wherein said hydrogen is provided on demand so that reaction pressure does not exceed about 200 psig.

17. A process in accordance with claim 1 wherein said functionally-substituted cis-olefinic compound is recovered in essentially pure form by:
(i) filtering the hydrogenation reaction mixture to give a filtrate; and
(ii) subjecting said filtrate to distillation under reduced pressure.

18. A process in accordance with claim 1 wherein said nickel boride is prepared by contacting at least one nickel compound selected from the group consisting of:
nickel acetate,
nickel fluoride
nickel chloride,
nickel bromide,
nickel iodide,
nickel nitrate,
nickel sulfate,
nickel acetylacetonate,
and mixtures of any two or more thereof, with at least one borohydride compound having the formula:
$M(BH_4)_n$; wherein M is a monovalent or divalent cation selected from the group consisting of:
$NR_4'-$; wherein each R' is independently $C_1$ through $C_{10}$ alkyl, cycloalkyl, aryl, aralkyl and alkaryl; alkali metals, and
alkaline earth metals; wherein n=1 if M is a monovalent cation and n=2 if M is a divalent cation.

19. A process for the preparation of a cis-olefinic halide having the formula:

$$H-(CR_2)_x-CH_2-CH=CH-CH_2-(CR_2)_y-CH_2-X$$

wherein x=0 through 20, y=1 through 20, each R is independently H, $C_1$ through $C_{20}$ alkyl, cycloalkyl, aryl, aralkyl, and alkaryl, and X is —Cl, —Br, or —I comprising the steps of:
(a) reaction of an α,ω-dihalide having the formula:

$$X-CH_2-(CR_2)_y-CH_2-X$$

wherein y, R and X are as defined above with a metal acetylide having the formula:

$$Me-C\equiv C-CH_2-(CR_2)_x-H$$

wherein x and R are as defined above and Me is Li or Na to give an acetylenic halide having the formula:

$$H-(CR_2)_x-CH_2-C\equiv C-CH_2-(CR_2)_y-CH_2-X$$

wherein x, y, R and X are as defined above; and (b) hydrogenation of the acetylenic halide obtained in (a) with hydrogen and a selective hydrogenation catalyst which comprises nickel boride on an inorganic oxide support to give said cis-olefinic halide; wherein said inorganic oxide support is selected from the group consisting of:
silica,
alumina,
silica-alumina,
aluminum phosphate,
zirconium phosphate,
titanium phosphate,
calcium phosphate,
magnesium phosphate,
magnesia-titania,
thoria,
titania,
zirconia,
and mixtures of any two or more thereof.

20. A process in accordance with claim 19 wherein the nickel metal content of said catalyst comprising nickel boride is present in a range of about 0.1 to about 40 wt. % based on total weight of support plus nickel boride and calculated as nickel metal.

21. A process in accordance with claim 19 wherein said cis-olefinic halide is recovered in essentially pure form by:
  (i) filtering the hydrogenation reaction mixture to give a filtrate; and
  (ii) subjecting said filtrate to distillation under reduced pressure.

22. A process in accordance with claim 19 wherein said nickel boride is prepared by contacting at least one nickel compound selected from the group consisting of:
nickel acetate,
nickel fluoride
nickel chloride,
nickel bromide,
nickel iodide,
nickel nitrate,
nickel sulfate,
nickel acetonylacetonate,
and mixtures of any two or more thereof, with at least one borohydride compound having the formula:
  $M(BH_4)_n$; wherein M is a monovalent or divalent cation selected from the group consisting of:
  $NR_4'$-wherein each R' is independently $C_1$ through $C_{10}$ alkyl, cycloalkyl, aryl, aralkyl and alkaryl;
  alkali metals, and
  alkaline earth metals;
wherein n=1 if M is a monovalent cation and n=2 if M is a divalent cation.

* * * * *